United States Patent [19]
Yorkgitis et al.

[11] Patent Number: 6,037,180
[45] Date of Patent: Mar. 14, 2000

[54] METHOD FOR MEASURING THE QUANTITY OF A POLYMERIC OR PRE-POLYMERIC COMPOSITION

[75] Inventors: Elaine M. Yorkgitis, St. Paul; Craig S. Chamberlain, Woodbury, both of Minn.

[73] Assignee: Minnesota Mining and Manufacturing Company, St. Paul, Minn.

[21] Appl. No.: 08/610,605

[22] Filed: Mar. 8, 1996

[51] Int. Cl.$^7$ .......................... G01N 15/06; G01N 27/00; G01N 27/82

[52] U.S. Cl. ................................. 436/56; 73/149; 73/582; 73/866; 324/71.1; 324/207.22; 324/219; 436/149

[58] Field of Search ........................ 436/56, 149; 73/582, 73/149, 866; 324/219, 226, 71.1, 207.22

[56] References Cited

U.S. PATENT DOCUMENTS

| | | | |
|---|---|---|---|
| 4,152,271 | 5/1979 | Eisenberg | 436/56 |
| 4,197,104 | 4/1980 | Krystyniak et al. | 436/56 |
| 4,197,220 | 4/1980 | Rembaum et al. | 436/55 |
| 4,582,534 | 4/1986 | Torobin . | |
| 4,618,525 | 10/1986 | Chamberlain et al. . | |
| 4,654,165 | 3/1987 | Eisenberg | 436/56 |
| 4,670,339 | 6/1987 | Frey . | |
| 4,906,497 | 3/1990 | Hellmann et al. . | |
| 4,944,185 | 7/1990 | Clark, Jr. et al. . | |
| 4,980,005 | 12/1990 | Scollard . | |
| 5,200,704 | 4/1993 | Clark, Jr. et al. . | |
| 5,206,096 | 4/1993 | Goldstein et al. . | |
| 5,272,216 | 12/1993 | Clark, Jr. et al. . | |
| 5,317,045 | 5/1994 | Clark, Jr. et al. . | |
| 5,327,081 | 7/1994 | Rudd et al. . | |
| 5,340,649 | 8/1994 | Roeker et al. . | |
| 5,447,592 | 9/1995 | Berce et al. . | |

FOREIGN PATENT DOCUMENTS

| | | |
|---|---|---|
| 0493946 | 7/1992 | European Pat. Off. . |
| 0 503 794 A1 | 9/1992 | European Pat. Off. . |
| 0 573 706 A1 | 12/1993 | European Pat. Off. . |
| WO 94/04623 | 3/1994 | WIPO . |
| WO 94/20585 | 9/1994 | WIPO . |
| WO 95/22639 | 8/1995 | WIPO . |

OTHER PUBLICATIONS

Giurgiutiu et al., SPIE vol. 2717 (1996) pp. 361–372, May 1996.

W.G. Clark Jr., Magnetic Tagging Monitors Bond Integrity and Thickness, Adhesives Age, Jun. 1992, pp. 22–26.

W.G. Clark Jr. et al., Tagging Lets You Test The Untestable, Advanced Materials & Processes, Apr. 1990, pp. 59–69.

"Elasticity and fracture in particulate composites with strong and degraded interfaces", May 1996, Lekatou et al., Journal of Materials Research, vol. 11, No. 5, pp. 1293–1304.

"Electrical Stability During Vibration And Electromagnetic Pulse Survivability Of Silver–Plated Glass Bead Filled EMI Shielding Gaskets", J.F. Walther, IEEE 1989 National Symposium on Electromagnetic Compatability (Catalog No. 89CH2736–7), May 23–25, 1989, pp. 40–45.

*Primary Examiner*—Jan Ludlow
*Attorney, Agent, or Firm*—Brian E. Szymanski

[57] ABSTRACT

A method for measuring the quantity of a polymeric or pre-polymeric composition within a given volume that includes combining the polymeric or pre-polymeric composition with a plurality of microparticles having a non-ferromagnetic or non-ferrimagnetic core provided with a coating that is ferromagnetic, ferrimagnetic, or conductive, to form an admixture in which the microparticles are substantially uniformly dispersed throughout the composition. The microparticles have a detectable electromagnetic characteristic which correlates with the amount of the composition within a given volume. The electromagnetic characteristic of the microparticles is then measured to determine the quantity of the composition within a given volume.

28 Claims, 7 Drawing Sheets

METHOD FOR MEASURING THE QUANTITY OF A POLYMERIC OR PRE-POLYMERIC COMPOSITION

BACKGROUND OF THE INVENTION

The invention relates to measuring the quantity of a polymeric or pre-polymeric composition within a given volume.

Processes for manufacturing polymeric compositions (e.g., adhesives such as structural adhesives) often require adding or combining precise amounts of pre-polymeric components forming these compositions, particularly where these components react together to form the composition. Devices dispensing these components can malfunction periodically and/or systematically, resulting in the deposition of an incorrect mix of the components. These malfunctions can significantly affect the quality of the resulting products.

It is also desirable to be able to measure the quantity of polymeric or pre-polymeric material in any given volume of an article incorporating the material. For example, in the case of a structural adhesive joining two substrates together, it is desirable to measure the thickness of the adhesive throughout the adhesive joint to determine whether the thickness is uniform. Non-uniformities can affect the performance of the joint, causing it to under perform in some circumstances.

SUMMARY OF THE INVENTION

In general, the invention features a method for measuring the quantity of a polymeric or pre-polymeric composition within a given volume that includes combining the polymeric or pre-polymeric composition with a plurality of microparticles having a non-ferromagnetic or non-ferrimagnetic core provided with a coating that is ferromagnetic, ferrimagnetic, or conductive, to form an admixture in which the microparticles are substantially uniformly dispersed throughout the composition. The microparticles have a detectable electromagnetic characteristic which correlates with the amount of the composition within a given volume. The electromagnetic characteristic of the microparticles is then measured to determine the quantity of the composition within a given volume.

As used herein, a "pre-polymeric composition" refers both to compositions whose molecular weight has not been sufficiently advanced to qualify as a polymeric composition (e.g., partially polymerized pre-polymeric syrups), as well as individual reactants in the form of monomers or oligomers that react with themselves or with other reactants to form a polymeric composition.

In preferred embodiments, the core of the microparticles is selected from the group consisting of glass bubbles, glass beads, glass fibers, fumed silica particles, fused silica particles, mica flakes, polymeric particles, and combinations thereof, with glass bubbles being particularly preferred. The coating (which may be provided over substantially all or a portion of the surface of the core) is preferably a ferromagnetic or ferrimagnetic material. Examples of suitable ferromagnetic or ferrimagnetic materials include nickel, cobalt, iron, alloys thereof and oxides thereof. Stainless steel coatings are particularly preferred. Other preferred coatings include electrically conductive coatings.

The dimensions of the microparticles preferably have a major dimension between about 10 micrometers and about 1 millimeter. The average thickness of the coating preferably ranges from about 0.1 nanometers to about 5 micrometers, more preferably from about 1 nanometer to about 200 nanometers. The amount of microparticles provided in the admixture preferably ranges between about 0.01 and 50% by volume.

In one preferred embodiment, the method is used to measure the quantity of a polymeric or pre-polymeric composition being dispensed, e.g., into a reaction mixture. According to this embodiment, the admixture containing the microparticles and pre-polymeric or polymeric composition is dispensed while measuring an electromagnetic characteristic of the microparticles to determine the quantity of the polymeric or pre-polymeric composition being dispensed.

In yet another preferred embodiment, a first polymeric or pre-polymeric composition and a second polymeric or pre-polymeric composition are combined to form a reaction mixture. At least one of the polymeric or pre-polymeric compositions is combined with the microparticles prior to combining the first and second polymeric or pre-polymeric compositions together. In a preferred embodiment, the electromagnetic characteristic of the microparticles in the reaction mixture is measured. The microparticles can be placed in both the first and second polymeric or pre-polymeric compositions. The microparticles in the first and second polymeric or pre-polymeric compositions can be different from each other. Another embodiment includes combining the microparticles with one of the polymeric or pre-polymeric compositions and measuring the electromagnetic characteristic of the reaction mixture to determine the ratio of the first and second polymeric or pre-polymeric compositions to each other.

In another preferred embodiment (useful, e.g., for quality control measurements), the admixture is deposited on or between a substrate and the electromagnetic characteristic of the microparticles is measured to determine the amount of the admixture deposited on the substrate. In this way, for example, variations in the thickness of the deposited material can be detected.

One example of a useful polymeric composition is an adhesive composition. Specific examples of preferred polymeric compositions include epoxy resins (e.g., base cured epoxies, acid cured epoxies, and addition cured epoxies), polyurethanes, acrylates, silicones, and phenolics.

The invention provides a low-cost, reliable method for measuring the quantity of a polymeric or pre-polymeric composition within a given volume using microparticle "tags" having a detectable electromagnetic characteristic. The microparticles are easily fabricated and are generally chemically inert and stable over reasonable periods of time.

Moreover, certain properties of the microparticles are very similar to their uncoated counterparts. For example, metal-coated glass microbubbles impart substantially the same Theological behavior and mechanical properties as their uncoated counterparts. Thus, the microparticles can be substituted virtually one-for-one for their uncoated counterparts on a volume basis without adversely affecting the properties of the final composition.

Other features and advantages of the invention will be apparent from the following description of the preferred embodiments thereof, and from the claims.

DESCRIPTION OF THE PREFERRED EMBODIMENTS

Materials

The preferred microparticles have a non-ferromagnetic or non-ferrimagnetic core and a coating that is ferromagnetic, ferrimagnetic, or electrically conductive. Generally, the microparticles can have a variety of shapes, including substantially spherical, elongated, or flat shapes. The shape may be selected to impart desired flow properties to the corresponding admixture given a selected concentration of microparticles in the admixture.

The dimensions of the microparticles can vary, but preferred microparticles have a major dimension smaller than 1 centimeter and more preferably from 10 micrometers to 1 millimeter. The coating preferably will have an average thickness between about 1 nanometer and 5 micrometers, and more preferably between about 1 and 200 nanometers. The coating can, but need not, cover the entire surface of the non-metal core. For example, the coating can form islands on the surface of the core, or the coating material can cover substantially all of the surface. Furthermore, the microparticles can have multiple coatings, partial coatings, or combinations thereof having different metals.

Suitable cores include materials typically used as reinforcing agents, rheology modifiers, or other additives in polymeric and pre-polymeric compositions. Examples include glass bubbles, glass beads, glass fibers, fumed silica particles, fused silica particles, mica flakes, polymeric particles, and combinations thereof. Preferred cores include hollow structures (e.g., in the form of bubbles) to minimize the overall amount of material added to the pre-polymeric or polymeric composition. Preferred core materials are glass microbubbles, e.g., commercially available from 3M Company, Saint Paul, Minn. under the trade name Scotchlite™. Preferred core materials include materials that are already within the compositions of interest so that the coated microparticles can be substituted for the uncoated microparticles in the composition. In this way, the composition can be tagged without requiring reformulation of the composition to obtain the desired rheological properties.

The coating for the microparticles generally can be any ferromagnetic, ferrimagnetic, or electrically conductive material that can be coated onto the surface of the microparticle core. A preferred coating should be chemically inert in the relevant compositions under the relevant conditions and stable with respect to degradation and leaching. Suitable ferromagnetic materials include iron, nickel, cobalt, alloys including one or more of these metals, and oxides including one or more of these metals. Appropriate electrically conductive materials include coatable metals, metal alloys and metal compounds, such as carbides, oxides, nitrides and silicides. Preferred conductive metals for use in coatings include copper, aluminum, and silver. The preferred material for the coating is stainless steel, which is both electrically conductive and ferromagnetic. If the coating material is ferromagnetic or ferrimagnetic, the core can be an electrically conductive, non-ferromagnetic, non-ferrimagnetic material, in which case the measurements will rely on the ferromagnetic or ferrimagnetic properties of the coating.

A variety of techniques can be used to apply the coating to the core. These techniques include sputtering, vapor deposition, electroless plating, and chemical vapor deposition.

The microparticles are added to a polymeric or pre-polymeric composition to form an admixture that is a tagged composition. The admixture will preferably include between about 0.01 and 50 percent by volume of the microparticles, and more preferably between about 0.1 and 30 percent by volume of the microparticles.

A wide variety of pre-polymeric and polymeric compositions can be used in conjunction with the microparticles. Preferred polymeric adhesive compositions include crosslinked systems such as epoxies (including base-cured epoxies, acid cured epoxies, and addition cured epoxies), polyurethanes, silicone resins, acrylate polymers, polysiloxanes, and phenolics, as well as blends of these types of systems. Hot melt adhesives include various polyolefins, polyesters, polyamides, polycarbonates, polyvinylacetates, higher molecular weight waxes, and related copolymers and blends. Additionally, applicable adhesive compositions would be those which are formed into films and tapes. Other useful polymeric compositions include sealants, plastisols, structural polymers used in gap filling and forming materials, coatings, fibers, gaskets, washers and laminates of various kinds. This invention is applicable to polymer compositions which are shaped by extrusion, molding, calendering, casting, and other processes into three-dimensional forms.

One suitable class includes adhesive compositions such as structural adhesives which include epoxy resins (e.g., derived from diglycidyl ethers of Bisphenol A or novolak resins). Structural adhesives are used in a variety of manufacturing situations including significant use in the automotive industry to bond parts together to reduce the need for welding. These materials, which are well-known, are typically prepared by reacting two or more pre-polymeric reagents with each other to form an intermediate "B-stage" resin, which is subsequently further cured to form the final product.

The pre-polymeric and polymeric compositions may contain various adjuvants designed to enhance the properties of the resin before or after curing, including reactive and nonreactive diluents, plasticizers, toughening agents, and coupling agents. Other materials which can be added to the composition include thixotropic agents to provide flow control (e.g., fumed silica), pigments, fillers (e.g., talc, silica, magnesium, calcium sulfate, beryllium aluminum silicate), clays, glass and ceramic particles (e.g., beads, bubbles, and fibers), and reinforcing materials (e.g., organic and inorganic fibers).

Use

The above-described microparticles can be used in a variety of measurement protocols. Measuring the electromagnetic properties of the microparticles provides a measure of the number of microparticles. The microparticles can be present in a known concentration within the composition to be measured to provide the quantity determination of the composition. Similarly, the microparticles can be used in a fixed concentration, where the quantity of the composition incorporating the microparticles is determined from a standard curve produced using material with the same fixed concentration.

If the microparticle-containing composition being measured is moving, the measurement will provide information on the flow and, correspondingly, the rate of deposition. If the composition is fixed relative to a substrate or container, the measurements can provide information on the distribution of the composition throughout the substrate or container.

One particularly useful application is in the context of dispensing polymeric or pre-polymeric compositions such as adhesives and pre-adhesive compositions. The material being dispensed can be a single polymeric or pre-polymeric composition that may or may not be later polymerized or crosslinked. This single composition would be used to form the admixture including the microparticles.

Alternatively, the material being dispensed can include two or more polymeric or pre-polymeric compositions that are mixed to form a curable resin, e.g., an intermediate "B-stage" resin. One or more of the components within the curable resin can be combined with a given volume fraction of microparticles. The electromagnetic properties of the microparticles can then be monitored to measure the amount of the reactant(s) dispensed into the reaction mixture. If one of two components is provided with microparticles, the coated microparticles in the reaction mixture can be measured to determine the quantity of reaction mixture. Based on the quantity measurements of the component and the reaction mixture, it can be determined if the two components were mixed in the proper ratio.

Alternatively, each component can be mixed with the same or different microparticles. Then, each component can be measured, with or without an additional measurement of the curable resin mixture, to determine whether the components have been mixed together in the correct ratio. Any variation from the desired amount can be noted and/or used to adjust the amount being dispensed. If microparticles with different electromagnetic characteristics, e.g., one ferromagnetic and the other non-ferromagnetic, are placed in the two different components, measurements on the two components being dispensed can determine if the correct component is being dispensed from the particular dispenser.

Another application involves use of the microparticles in the non-destructive testing of articles incorporating a polymeric or pre-polymeric composition. The measurements can be used to determine a variety of properties of the composition within the article, including thickness, integrity, orientation, and continuity. Similarly, a map can be obtained indicating the location of the composition. For example, in the case of structural adhesives forming a bond line to join two parts together, the properties of the bond line can be examined.

Either the electrical or the magnetic properties of the microparticles can be used to make the measurement. For example, in the case of ferromagnetic or ferrimagnetic microparticles, magnetic permeability can be measured. Magnetic permeability is a function of the number of ferromagnetic microparticles and the amount of metal coating on the microparticles. It can be measured using an a.c. magnetic hysteresis looper, e.g., a Gerard Electronic MH looper™ operating at a frequency of 10 kHz and an applied field strength of 10 gauss. Typically, the magnetic field is applied with a frequency between 1 and 10 kHz.

Alternatively, inductive reactance can be measured using an eddy current instrument (e.g., a Nortec 19e$^{II}$ Eddyscope ™, an impedance plane eddy current instrument, equipped with a Nortec OD/100 kHz/A/0.682" probe) to measure the quantity of microparticles (and thus the quantity of prepolymeric or polymeric composition) within a given volume. With proper calibration the vertical response of the eddyscope is proportional to the inductive reactance; this response is hereinafter referred to as the inductive reactance. The inductive reactance, i.e., the eddyscope response, is approximately proportional to the loading of the microparticles and coating thickness on the individual microparticles.

Another way of performing the measurement is by measuring the dielectric properties of the microparticles. Electrically conductive coatings on the microparticles increase the dielectric constant, which is related to microparticle loading. This can be determined, for example, by measuring the capacitance of a parallel plate capacitor containing the microparticles. An advantage of the dielectric measurement approach over the magnetic permeability approach in certain applications is that the magnetic response is related to the amount of magnetic material coated onto the microparticles, while the dielectric constant is approximately independent of coating thickness. Therefore, much thinner electrically conductive coatings can be used when the dielectric measurements are used.

Other aspects of the electromagnetic properties can be exploited to perform the measurements. For example, certain metals can scatter x-rays sufficiently, so x-ray transmission measurements can be used to quantify the amount of metal-coated microparticles present within a material. Alternatively, coatings can be selected to minimize interference with x-ray transmission so that articles can be examined with x-rays with minimal interference by the coated microparticles.

In addition, microwave or inductive heating methods can be used to heat the microparticles, after which the associated infrared emissions can be measured to quantify the amount of microparticles (and thus the amount of polymeric or pre-polymeric composition).

The invention will now be described by way of the following examples.

EXAMPLES

Example 1

This example demonstrates that glass bubbles can be coated with a very thin magnetic stainless steel coating.

K37 Scotchlite™ glass bubbles (sold by 3M, Saint Paul, Minn.) were sputter coated with 304 stainless steel according to the procedure described generally in U.S. Pat. No. 4,618,525, incorporated herein by reference. In this specific case, a 304 stainless steel target was dc magnetron sputtered for 7.0 hours at 8.0 KW at an argon sputtering gas pressure of 5 millitorr onto 415 grams of K37 Scotchlite glass bubbles. The 304 stainless steel sputter target was non-magnetic austenitic face centered cubic, but deposits as the magnetic ferritic body centered cubic form. These materials have been described in a publication by T. W. Barbee, B. E. Jacobson and D. L. Keith, 63 Thin Solid Films 143–150 (1979).

The resulting stainless steel coated bubbles had an iron content of 7.86% by weight (determined by inductively coupled plasma emission spectroscopy), corresponding to 11.2% by weight stainless steel (which is 70% by weight iron). The surface area of the glass bubbles was determined by the B.E.T. method to be 0.55 square meters per gram. The density of the coated bubbles was measured using a Beckman Model 930 air comparison pycnometer. The density of the uncoated bubbles was 0.36 g/cc, and that of the coated bubbles was 0.41 g/cc.

The metal coating thickness can be calculated from the relevant relationship described in U.S. Pat. No. 5,409,968. In this case, the coating thickness was determined to be 29 nm.

Example 2

This example demonstrates the effect of volume loading of stainless steel coated bubbles on inductive reactance.

Glass bubbles with a 29 nm thick stainless steel coating were used. Devcon™ 5-minute epoxy (ITW Devcon, Danvers, Mass.) was used to prepare samples with various volume loadings of coated bubbles. This mixture was placed in 80 mm long Pyrex™ glass tubes with 13.2 mm inner diameter and a 16.0 mm outer diameter.

The inductive reactance was then measured using a Nortec Eddyscope. Several variables can be optimized on the Eddyscope. For a given probe, these are (1) frequency, (2) gain, and (3) probe drive voltage. The rotation ("Rot" knob on the instrument) was used to calibrate the Eddyscope so that displacement along the y-axis provided a measure of inductive reactance. Inductive reactance in unscaled units was read from the Eddyscope display. Barium ferrite, which is magnetic but not significantly electrically conductive, was chosen as a calibrating material. With a frequency fixed at 100 kHz, rotation was varied until introduction of the barium ferrite sample resulted in a purely vertical response on the Eddyscope screen (rotation=311 degrees).

Figure 1:
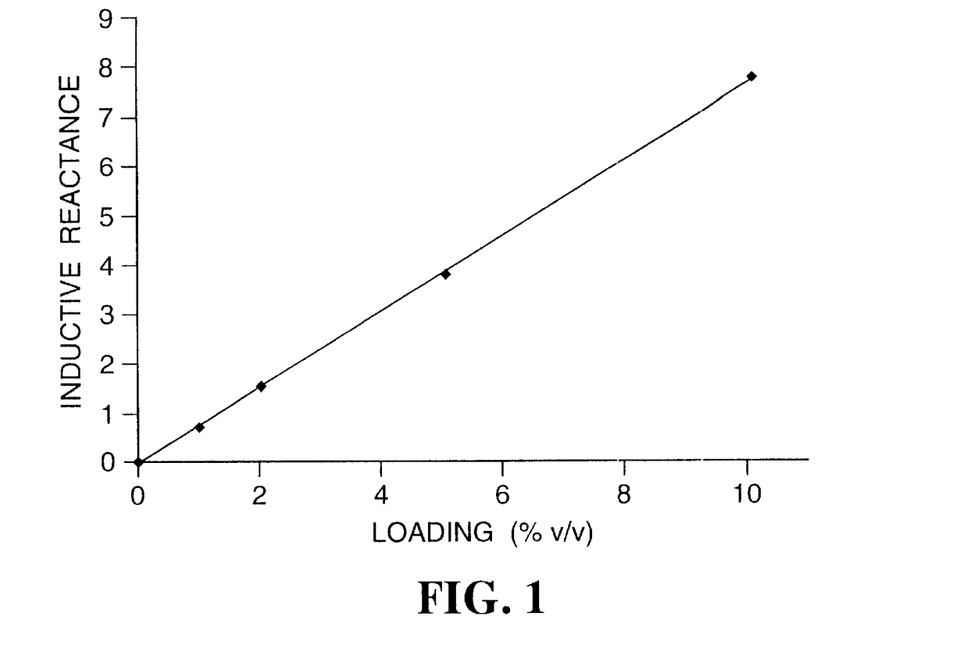
FIG. 1 is a plot of inductive reactance versus loading of coated microparticles in percent volume fraction.

The Eddyscope settings included a gain of 76.0 dB with probe drive of "Mid." Reactance versus microparticle loading is plotted in FIG. 1. This illustrates the linear relationship between the two variables. It shows that the reactance can be used as a good measure of the bubble content.

Example 3

This example demonstrates the effect of coating thickness on inductive reactance.

Procedures similar to that in Example 1 were carried out to make stainless steel coated glass bubbles with coating thicknesses of 59 and 86 nanometers. The density for each of the coated bubble samples was 0.44 and 0.49 g/cc, respectively. In addition, glass bubbles with a 29 nm thick stainless steel coating prepared as in Example 1 were used.

Figure 2:
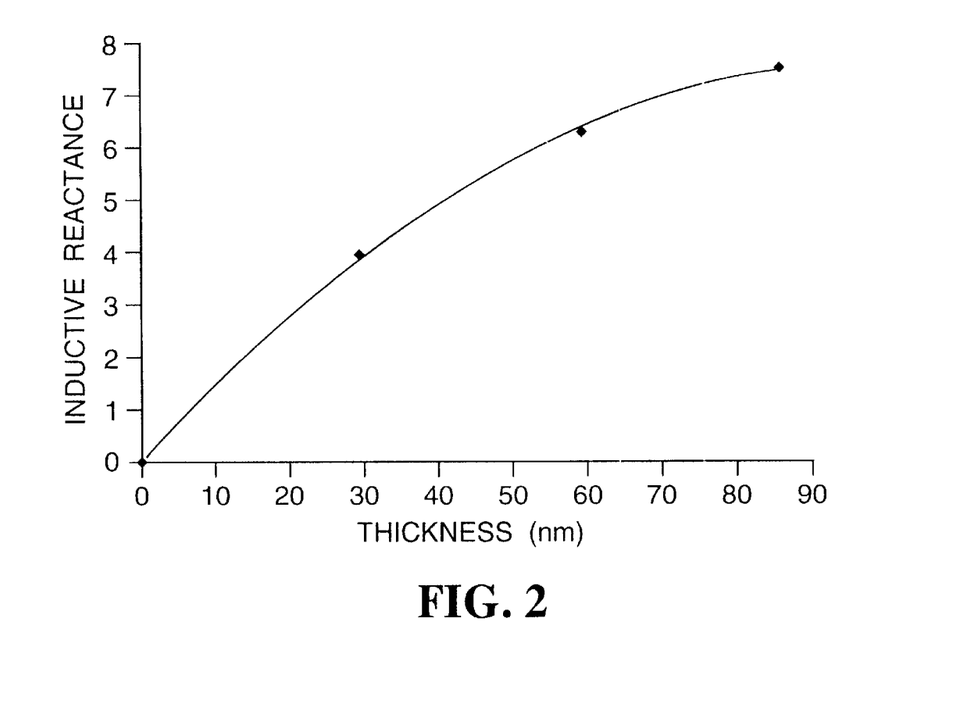
FIG. 2 is a plot of inductive reactance versus coating thickness.

The Eddyscope parameters were set as in Example 2 except that the gain was 70.0 dB. Test samples in Devcon 5-minute epoxy were prepared at 10% volume loading for each of the three samples of coated bubbles. The inductive reactance was measured and is plotted as a function of the stainless steel coating thickness in FIG. 2. The inductive reactance increases monotonically with stainless steel thickness.

Example 4

In this example, the use of acicular particles is demonstrated.

Milled glass fibers (Type 731 DD 1/16 inch milled glass fibers) were obtained from Owens/Corning Corporation (Anderson, S.C.). They had an aspect ratio range of approximately 1 to 40, with a fiber diameter of 15.8 microns. Stainless steel was deposited onto 1570 grams of these fibers for 20 hours at 8.0 kW in the manner previously described in Example 1.

The weight percent iron was determined to be 6.2%, corresponding to 8.9% by weight stainless steel. The surface area of the uncoated fibers was 0.10 square meters per gram.

The stainless steel coated milled glass fibers were dispersed in Devcon 5-minute epoxy at a volume loading of 10%. The mixture was placed in glass tubes, as described in Example 2. The Eddyscope was set to a gain of 68.0 dB with Probe Drive on High. The inductive reactance was determined to be 8.9.

Example 5

In this example, the use of a magnetic cobalt coating is demonstrated.

Milled glass fibers were sputter coated with cobalt, as described in Example 1, using a MAK 3 inch Magnetron Sputtering Source (US Thin Film Products Inc, Campbell, Calif.). The weight percent cobalt was determined to be 5.6%, corresponding to a coating thickness on the fibers of 67 nm.

The cobalt coated milled glass fibers were dispersed at 10% by volume in Devcon 5 minute epoxy and loaded into a glass tube as described in Example 4. The Eddyscope was set to the same conditions as Example 4 except that the gain was raised to a value of 80.0 dB. The inductive reactance was determined to be 9.6.

Example 6

In this example, flat, flake shaped particles were used. Silicone rubber, rather than epoxy, was the polymer component. Stainless steel was deposited onto 460 grams of 200HK Suzorite™ mica flakes (Suzorite Mica, Inc., Hunt Valley, Md.) for 13.5 hours at a power of 8.0 kW in the manner described in Example 1.

The stainless steel-coated mica flakes were dispersed at a volume loading of 10% into RTV 615 ™, a silicone rubber available from Dow Corning Corporation. This was loaded into a glass tube as described in Example 3. The Eddyscope was set to the same conditions as Example 4 except that the gain was set to a value of 60.0. The inductive reactance was determined to be 8.4.

Example 7

This example illustrates the relationship between the measured magnetic permeability and the stainless steel coating thickness on the glass bubbles.

The three stainless steel-coated bubble samples described in Example 3 were combined with Devcon 5 minute epoxy at a volume loading of 10%. The material was used to fill tubes (straws) with a 5 mm internal diameter to a depth of 70 mm. The permeability was determined from a hysteresis loop obtained using a Gerard Electronic MH looper operating at a frequency of 10 kHz and an applied field strength of 10 gauss. The permeability was calculated from the maximum applied field in gauss and the maximum magnetization in emu/cc. A BH looper could also be used.

Figure 3:
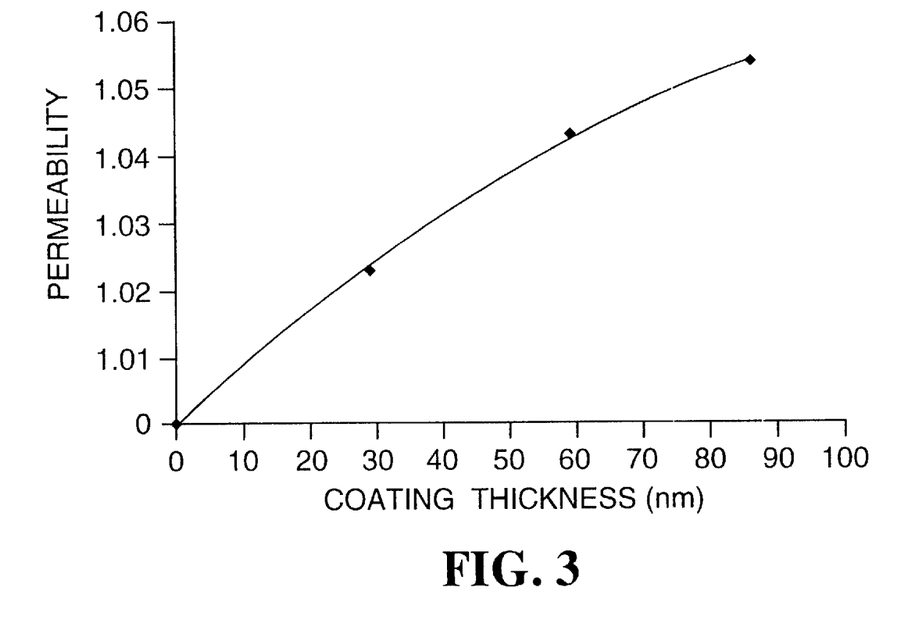
FIG. 3 is a plot of permeability versus coating thickness.

The permeability is plotted versus stainless steel coating thickness in FIG. 3. Permeability is seen to monotonically increase with coating thickness. This demonstrates that these very thin magnetic coatings can provide significant and reproducible permeabilities. The higher coating thicknesses give higher permeabilities.

Example 8

Figure 4:
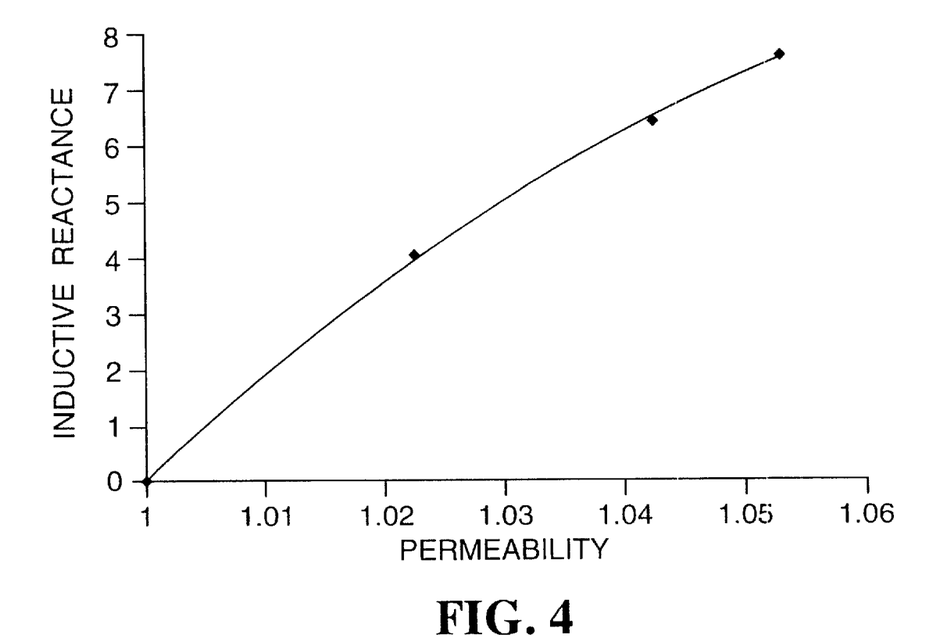
FIG. 4 is a plot of inductive reactance versus permeability.

This example demonstrates that the inductive reactance for coated particles is directly related to their magnetic permeability. Magnetic permeability is a fundamental magnetic property of the coated microparticles incorporated into an adhesive. Magnetic permeability is related to the Eddyscope response, which is the inductive reactance. To demonstrate this relationship, the magnetic permeability measurements of Example 7 are plotted in FIG. 4 against the inductive reactance measurements of Example 3 using the same coating thicknesses of stainless steel on glass bubbles. The inductive reactance is monotonic, and almost proportional to the permeability.

Example 9

This example demonstrates the use of the magnetic coated microparticles within an adhesive for non-destructive testing. This could be used as a form of non-destructive testing to determine the continuity of the adhesive bondline.

Devcon 5 minute epoxy was used to make an adhesive having a 26% volume loading of glass bubbles with a 29 nm thick stainless steel coating prepared as in Example 1. About 1% by volume of 60–100 micron diameter glass beads were added as spacers. A bead of this material was laid onto a strip of aluminum measuring 0.61 mm thick, 19 mm wide, and 31 cm long. In the middle, the adhesive was removed from a span of about 3 cm. An identical piece of aluminum was pressed onto the adhesive on the first piece to make an aluminum-epoxy-aluminum sandwich structure. Adhesive which exuded from both edges of the structure was removed after the adhesive had cured.

Figure 5:
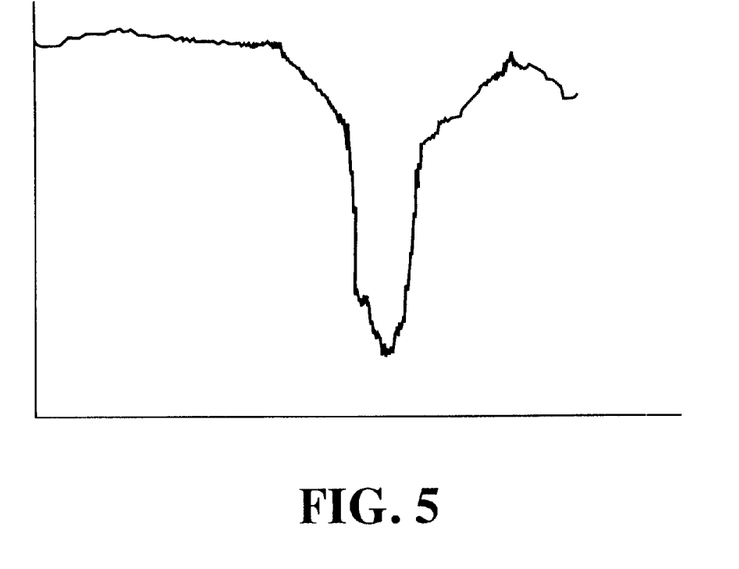
FIG. 5 is an Eddyscope scan of an aluminum-epoxy-aluminum structure.

A Nortec SPO-5781™ 1 kHz–50 kHz edge probe was used to scan the structure. The Eddyscope was set at 5 kHz with 0 degrees rotation and probe drive Hi. The scan is presented as a screen print in FIG. 5. The gap in the adhesive between the two aluminum pieces is clearly shown.

Example 10

This example demonstrates the use of a simple solenoid coil in place of an eddy current instrument, such as an Eddyscope, to determine loading of coated microbubbles.

A solenoid coil was prepared by winding size 36 (0.127 mm diameter) insulated copper wire onto a 19.0 mm o.d. glass tube. The coil had 333 turns in four layers over a length of 3.0 cm. The two leads from the coil were connected to a Tenmark 72-370™ digital LCR meter. An LCR meter is a hand-held device capable of measuring inductance, capacitance, or resistance when attached to an appropriate sensing device. 80 mm long, 16.0 mm outer diameter glass tubes containing Devcon epoxy with various loadings of glass bubbles provided with 29 nm-thick stainless steel coatings were inserted into a tube (centered in the coil region), which had a 16.5 mm inner diameter.

Figure 6:
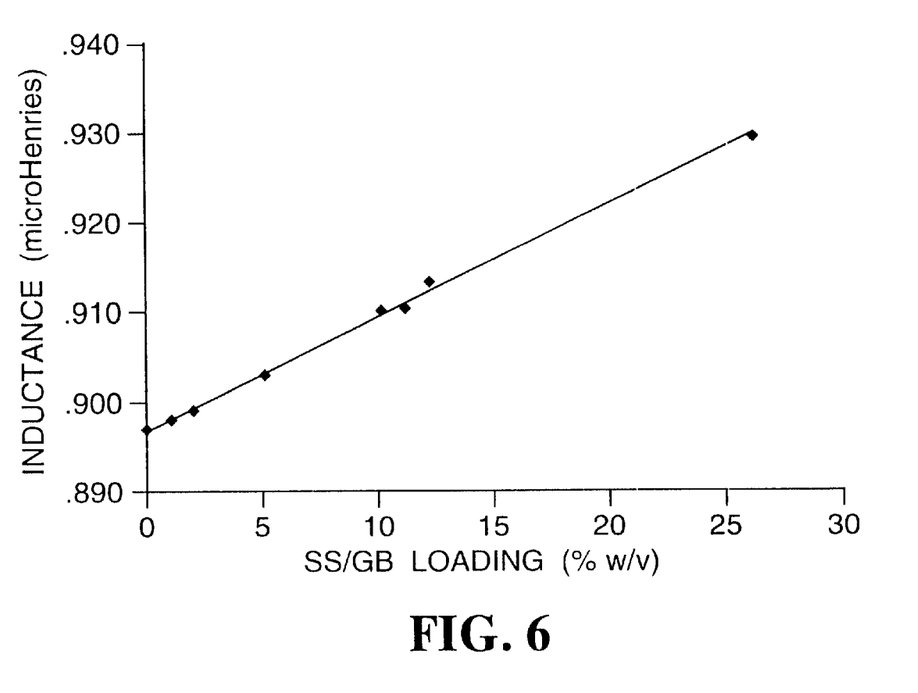
FIG. 6 is a plot of inductance versus coated microparticle loading in percent volume fraction.

The inductance was read off the LCR meter and is plotted versus volume loading in FIG. 6. The approximate linear relationship between inductance and loading demonstrates the fundamental relationship between the two. This also shows that equipment other than an eddy current instrument can be used in sensing loadings in the adhesives containing the microparticles.

Example 11

This example demonstrates that capacitive, rather than inductive, measurements can be used to determine microparticle loading in adhesives.

A two-plate capacitor was made for detecting the capacitance of an adhesive material. Two pieces of adhesive-backed copper foil were cut to form rectangles 2.0 cm wide×3.0 cm long. These were affixed to the outside of a glass tube of the same dimensions as the larger glass tube in Example 10. They were affixed opposing one another so as to form a curved-plate rather than parallel-plate capacitor. Electrical leads from each plate were connected to the same LCR meter described in Example 10. This sensing apparatus was loaded with various samples of adhesives containing coated microparticles as described in Example 10.

Figure 7:
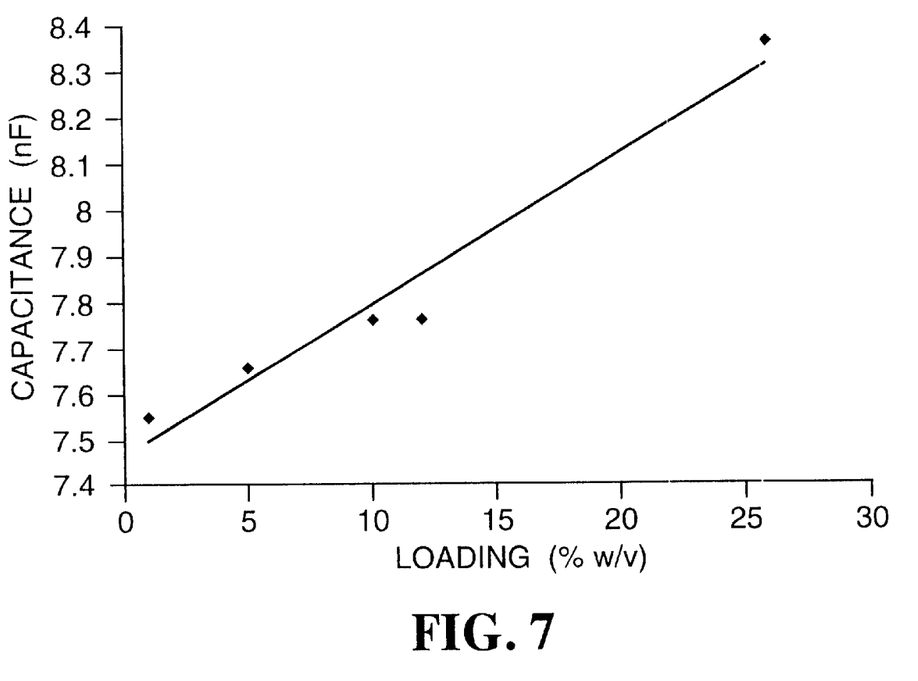
FIG. 7 is a plot of capacitance versus coated microparticle loading in percent volume fraction.

The capacitance was read off the LCR meter and is plotted versus loading of the coated microparticles in the adhesive in FIG. 7. The approximate linear relationship between the two demonstrates that measurement of capacitance provides another means of determining concentration.

Example 13

This example demonstrates the ability of an object made with a material incorporating microparticles to be mapped using an Eddyscope. It also demonstrates the use of a thermoplastic, rather than thermoset, resin.

A rectangular plastic tray was obtained from 3M Company, St. Paul, Minn. It is identified as Thin PQFP™ 132 21002-203. It is 32.3 cm wide by 0.85 cm thick. It contains 24% by volume stainless steel-coated milled glass fibers dispersed in Mindel S1000, a thermoplastic resin obtained from Amoco Chemical Company, Chicago, Ill. A Nortec S-300™ Hz-10 kHz/0.62 surface probe was oriented vertically 1 mm above the surface of the tray in such a manner as to allow the tray to be scanned under it. The Eddyscope was set with a frequency of 1.0 kHz, a gain of 90 dB, a probe drive "Hi," and rotation 18 degrees. The tray was manually scanned under the probe with inductive reactance versus time being recorded.

Figure 8:
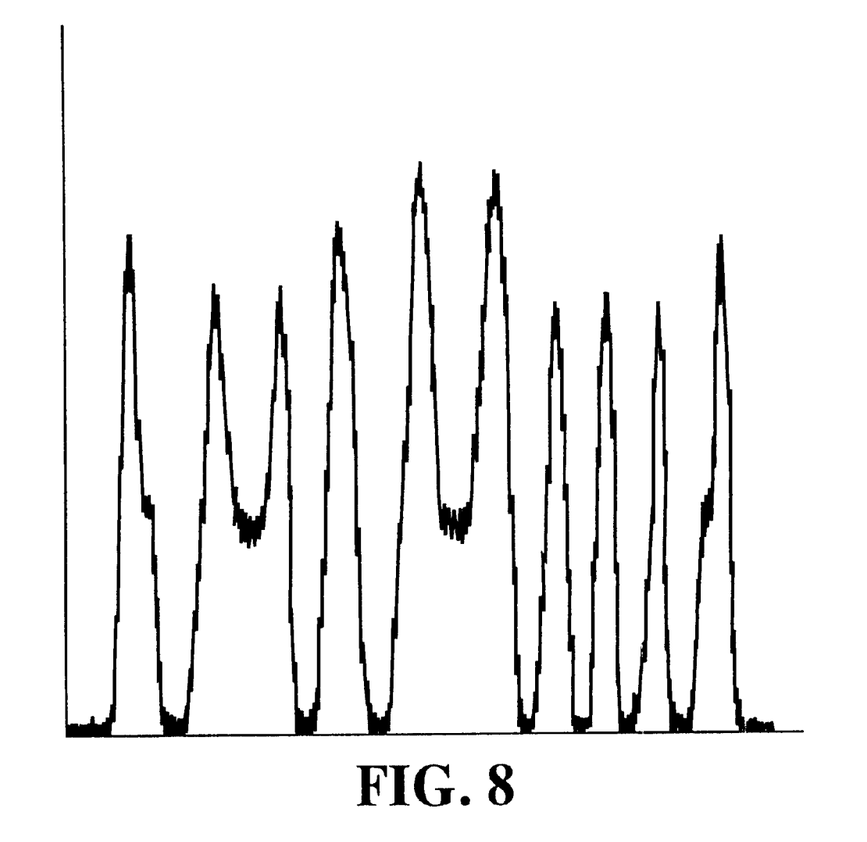
FIG. 8 is an Eddyscope scan of a plastic tray.
Figure 9:
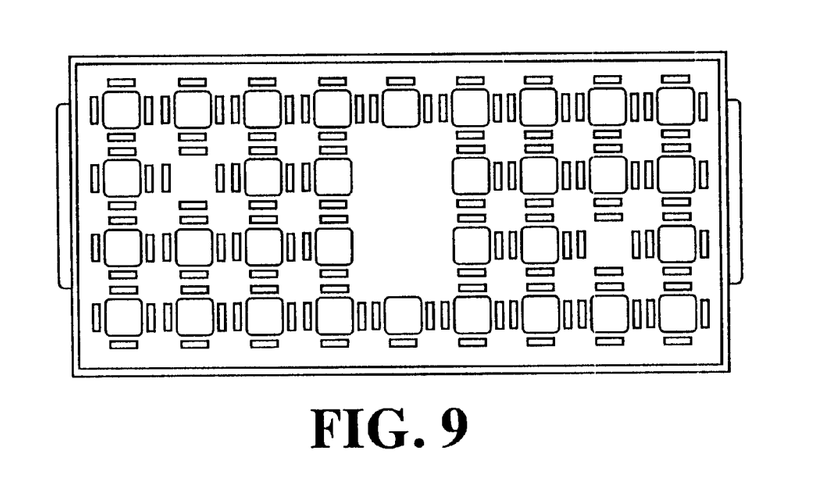
FIG. 9 is a physical map of the tray of FIG. 8 made using the Eddyscope readings.

The scan (FIG. 8) shows a map of the presence of high spots and voids in the tray. A physical map of the tray from the top side is also given here for comparison in FIG. 9. The scan was made in a straight line from one end of the tray to the other on the second row from the top, as indicated by the horizontal arrow.

Example 13

This example demonstrates the ability of a material incorporating microparticles to be mapped using capacitance, rather than an Eddyscope.

A parallel-plate capacitor was set up for the purpose of scanning the tray of Example 12. The top electrode was a rectangle measuring 1.4 cm by 1.0 cm and the bottom electrode measured 15 cm by 15 cm. The spacing between the electrodes was 0.8 cm. The capacitance was measured using the meter described in Example 10.

Figure 10:
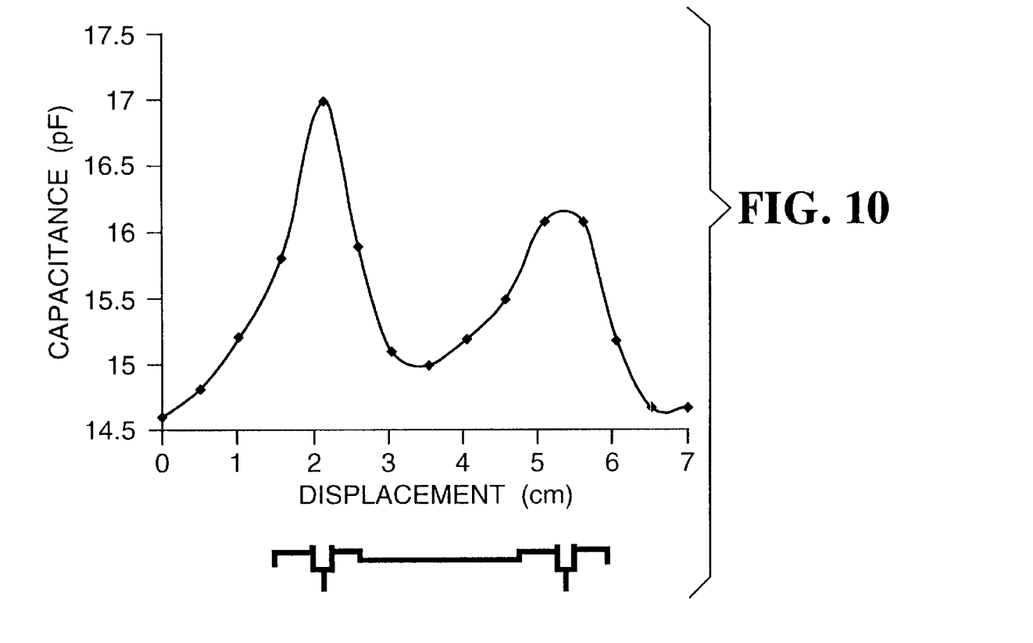
FIG. 10 is a plot of capacitance versus displacement along a width of the tray of FIG. 8 with a schematic of the cross section of the tray shown below the plot.

The tray was moved through the sensing capacitor, with the capacitance recorded at 0.5 cm increments. The capacitance map is shown in FIG. 10 along with a schematic cross section of the tray. The voids, peaks, and valleys on the surface of the tray are clearly indicated in this scan (within the resolution of the top electrode).

Example 14

This example demonstrates how an off-ratio mixing event can be detected when the adhesive contains coated glass bubbles. The following two component adhesive formulation was prepared using glass bubbles with a 29 nm stainless steel coating:

|  | Parts (g) | Density (g/cc) | Volume |
| --- | --- | --- | --- |
| Part B |  |  |  |
| Epon 828 DGEBA | 80 | 1.17 | 68.38 |
| Heloxy 107 epoxy diluent | 20 | 1.09 | 18.35 |
| TS-720 fumed silica | 2 | 1.8 | 1.11 |
| 0.25-mm glass beads | 3 | 2.5 | 1.20 |
| GP-71 fused silica | 20 | 2.2 | 9.09 |
| 29 nm SS-coated glass bubbles | 21.7 | 0.41 | 52.93 |
| Totals | 146.7 |  | 151.05 |
| Part A |  |  |  |
| Polyamidoamine | 40 | 1.0 | 40.00 |
| H221 amine | 6 | 0.98 | 6.12 |
| Ancamine K54 tertiary amine | 8 | 0.97 | 8.25 |
| ATBN 1300x16 liquid rubber | 10 | 0.96 | 10.42 |
| TS-720 fumed silica | 3 | 1.8 | 1.67 |
| GP-71 fused silica | 20 | 2.2 | 9.09 |
| Totals | 87 |  | 75.54 |

Epon 828™ is a diglycidyl ether of bisphenol A available from Shell Chemical Company. Heloxy 107 is a diglycidyl ether of cyclohexane available from Shell Chemical Company. TS-720 is a hydrophobic fumed silica available from Cabot Corporation. The glass beads have a nominal diameter of 0.01 inches, available from Cataphote, Inc. GP-71™ is an amorphous silicon dioxide available from Harbison-Walker Corporation. The glass bubbles are hollow glass microspheres available from 3M Corporation. The polyamidoamine is an amine-terminated polyamide. H221 is 4,7,10-trioxatridecane 1,3-diamine available from BASF. Ancamine K54 is 2,4,6-trimethyaminomethyl phenol available from Air Products Chemical, Inc. ATBN 1300x16 is acrylonitrile-terminated butadiene liquid rubber available from B. F. Goodrich Company.

The proper mix ratio of this adhesive by weight is 146.7/87 or 1.69 B:A, obtained by dividing the formula weight of Part B by the formula weight of Part A. (By volume, by a similar procedure, the volume mix ratio is 151.05/75.54 or 2.0 B:A). By increasing or decreasing 1.69 by 10%, it can be determined that a B:A mix ratio of 1.86:1.00 represents a plus 10% off-ratio while 1.52:1.00 represents a minus 10% off-ratio.

Mixtures of the above Part B and Part A were prepared at B:A by weight mix ratios of 1.52:1.00, 1.69:1.00, and 1.86:1.00; degassed while being mixed; and pulled by vacuum into three separate half-inch static mixing nozzles. After being filled, the nozzles were inserted into the eddy current probe as described in Example 2.

The response of the Eddyscope was somewhat more consistent when the mixing elements were removed from the static mix nozzles because filling of the nozzles is more uniform without the mixing elements. In a dynamic situation where many gallons of mixing adhesive are pumping through a given nozzle, a steady-state response could be achieved.

Figure 11:
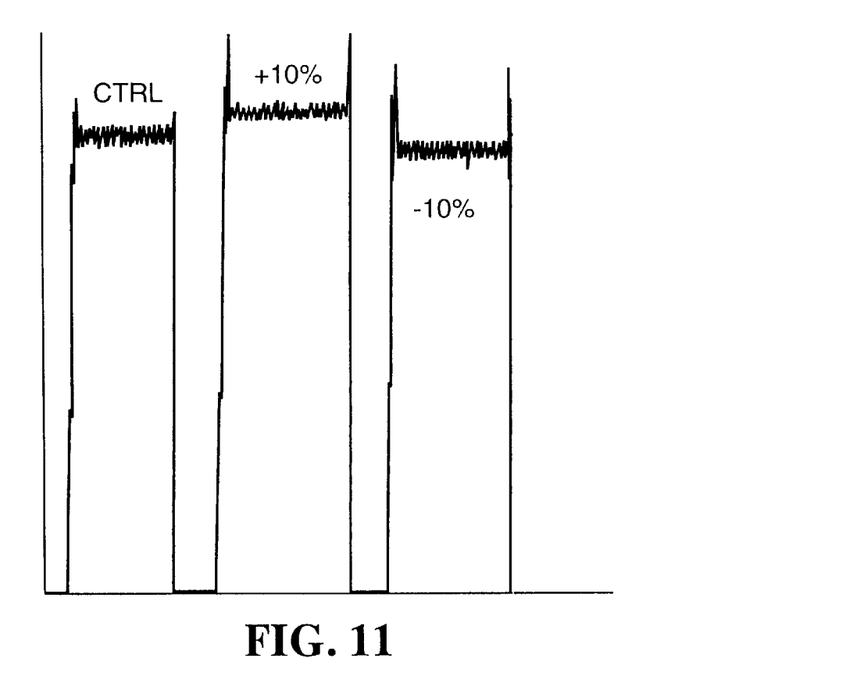
FIG. 11 is an Eddyscope scan indicating the different reading obtained with different ratios of one component of an adhesive mixed with a second component of an adhesive.

To simulate this dynamic response, the nozzle is moved back and forth in the probe. As FIG. 11 demonstrates, the Eddyscope responses corresponding to adhesives mixed under the proper (control) mix ratio, −10% off-ratio, and +10% off-ratio are readily differentiated from each other. The measured responses can provide a process window within which mix ratio can be established and maintained using an adhesive containing coated glass bubbles.

Example 15

This example demonstrates the substitutiion of varying amounts of coated glass bubbles for already present plain glass bubbles.

A two component adhesive (16-1) was made using uncoated glass bubbles, and corresponding versions were made (16-2 through 16-6) by substituting for some or all of the plain glass bubbles in the B adhesive component with stainless steel coated glass bubbles having a 29 nm stainless steel coating. The B adhesive component contained a 0.35 volume fraction of glass bubbles.

|  | Parts by Weight (g) in B Component | | | | | |
| --- | --- | --- | --- | --- | --- | --- |
|  | 16-1 | 16-2 | 16-3 | 16-4 | 16-5 | 16-6 |
| Epon 828 DGEBA | 80 | 80 | 80 | 80 | 80 | 80 |
| Heloxy 107 epoxy diluent | 20 | 20 | 20 | 20 | 20 | 20 |
| TS-720 fumed silica | 2 | 2 | 2 | 2 | 2 | 2 |
| 0.25-mm glass beads | 3 | 3 | 3 | 3 | 3 | 3 |
| GP-71 fused silica | 20 | 20 | 20 | 20 | 20 | 20 |
| K37 glass bubbles | 19.6 | 19.4 | 18.6 | 17.6 | 9.8 | 0 |
| SS-coated bubbles (29 nm coating) | 0 | 0.2 | 1.1 | 2.2 | 10.9 | 21.7 |
| Total formula weight (g) | 144.6 | 144.6 | 144.7 | 144.8 | 145.7 | 146.7 |
| B:A by Weight | 1.66:1 | 1.66:1 | 1.66:1 | 1.66:1 | 1.67:1 | 1.69:1 |
| B:A by Volume | 2:1 | 2:1 | 2:1 | 2:1 | 2:1 | 2:1 |
| Total Volume Fraction Bubbles on B Side | 0.35 | 0.35 | 0.35 | 0.35 | 0.35 | 0.35 |
| Volume Fraction of Coated Bubbles | 0.0 | 0.0035 | 0.0175 | 0.035 | 0.175 | 0.35 |
| Substitution Level Based on Total Bubble Volume (percent) | 0 | 1 | 5 | 10 | 50 | 100 |

Part A is as given below and is used in the given mix ratio with each of the above Part Bs to form a 2:1 mixture by volume. The nature of the ingredients of the A and B compositions are described further in Example 14.

| Part A | |
| --- | --- |
| Polyamidoamine | 40 |
| H221 amine | 6 |
| Ancamine K54 Tertiary Amino | 8 |
| ATBN 1300x16 Liquid Rubber | 10 |

| -continued | |
|---|---|
| Part A | |
| TS-720 Fumed Silica | 3 |
| GP-71 Fused Silica | 20 |
| Totals | 87 |

The volume fraction of total glass bubbles was kept as close as possible to a constant value for all B components using calculations involving the 0.37 g/cc density of the uncoated glass bubbles and the 0.41 g/cc density of the stainless steel coated glass bubbles. The parts of all bubble components were rounded to the nearest 0.1 g.

Using the listed mix ratios and a multiplication factor of 30, samples of the B components 16-1 through 16-6 were mixed under vacuum with the appropriate amount of the A component and deposited into flat-bottomed plastic weighing dishes. The component mixtures were allowed to cure at room temperature into a solid mass about 2.5 inches in diameter and at least 0.5 inches thick. After cure, the dish was peeled off of each hardened adhesive to present a flat surface which was interrogated using a flat surface probe, Nortec #954769, S/1 kHz–50 kHz/0.31. The Eddyscope was set at a frequency of 50 kHz, a gain of 67.0, and a rotation of 64 degrees.

Figure 12:
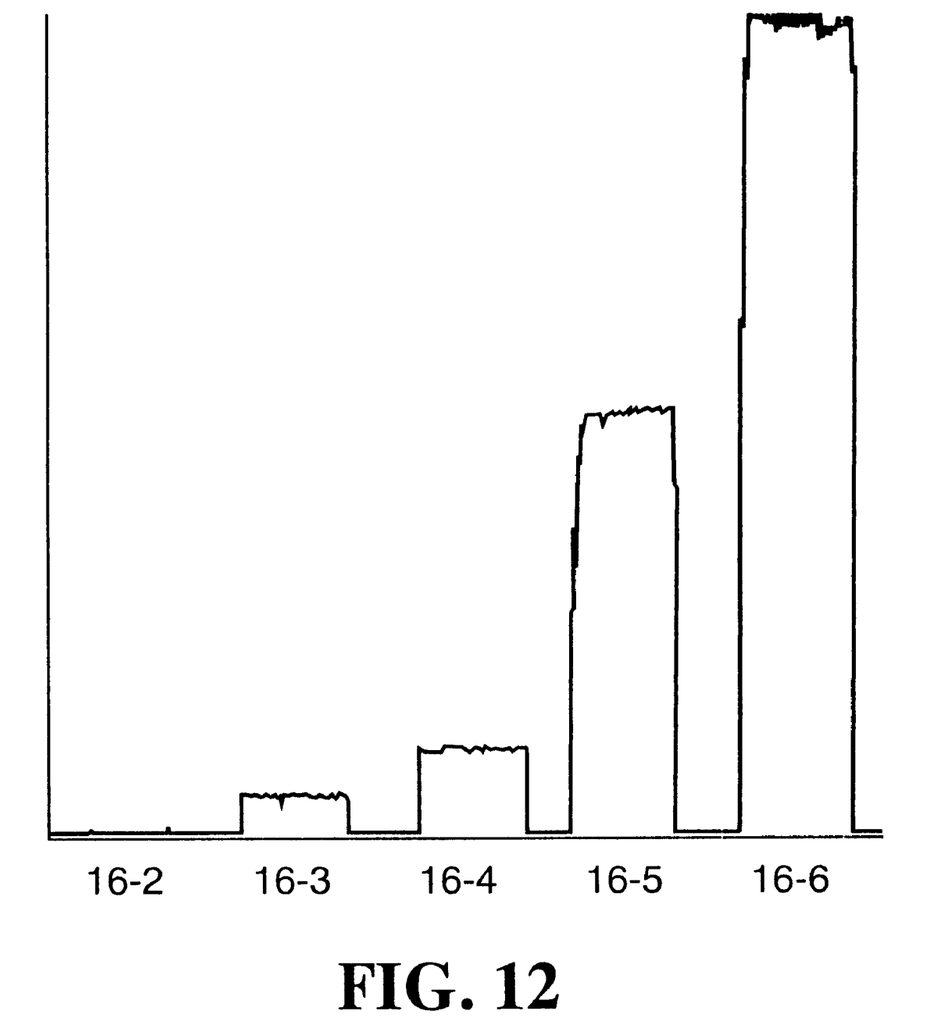
FIG. 12 is an Eddyscope scan indicating the different readings obtained from a volume of composition containing various loadings of coated microparticles.

Nulling in air and setting the surface probe against the flat bottoms of each of the molded samples containing coated glass bubbles in turn produced the results shown in FIG. 12. (The signal for the 16-2 material is weak due to the desire to fit data for all samples on the same screen/chart but could be increased by setting gain higher than 67.0.) The data clearly shows the systematic fashion in which the signal increases with increasing substitution of coated bubbles for uncoated bubbles with, for example, the signal for 10% substitution being approximately twice that for 5%, the signal for 50% being approximately five times that for 10%, and so on. The sample made using 16-1 mixed with Part A gave no measurable Eddyscope response.

Equivalents

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method for measuring the quantity of a polymeric or pre-polymeric composition within a given volume comprising the steps of:
   (a) combining said polymeric or pre-polymeric composition with a plurality of microparticles comprising a non-ferromagnetic or non-ferrimagnetic core provided with a coating that is ferromagnetic, ferrimagnetic, electrically conductive or a combination thereof to form an admixture in which said microparticles are substantially uniformly dispersed throughout said composition,
   said microparticles having a detectable electromagnetic characteristic which correlates with the amount of said composition within a given volume; and
   (b) measuring said electromagnetic characteristic of said microparticles to determine said quantity of said composition within a given volume.

2. The method of claim 1, wherein said core of said microparticles is selected from the group consisting of glass bubbles, glass beads, glass fibers, fumed silica particles, fused silica particles, mica flakes, polymeric particles, and combinations thereof.

3. The method of claim 1 wherein said core of microparticles comprises a glass bubble.

4. The method of claim 1 wherein said coating comprises an electrically conductive coating.

5. The method of claim 1 wherein said coating comprises a ferromagnetic or ferrimagnetic coating.

6. The method of claim 1 wherein said coating comprises stainless steel.

7. The method of claim 1 wherein said microparticles comprise metal-coated glass bubbles.

8. The method of claim 1 wherein said coating comprises a ferromagnetic or ferrimagnetic composition selected from the group consisting of nickel, iron, cobalt, alloys thereof and oxides thereof.

9. The method of claim 1 wherein said microparticles have a major dimension between about 10 micrometers to about 1 millimeter.

10. The method of claim 1 wherein said coating has an average thickness ranging from about 0.1 nanometers to about 5 micrometers.

11. The method of claim 1 wherein said coating has an average thickness ranging from about 1 nanometers to about 200 nanometers.

12. The method of claim 1 wherein said coating is in the form of a substantially continuous coating on said core.

13. The method of claim 1 wherein said admixture comprises between about 0.01 and 50% by volume of said microparticles.

14. The method of claim 1 comprising dispensing said admixture while measuring the electromagnetic characteristic of said microparticles to determine the quantity of said polymeric or pre-polymeric composition in said admixture being dispensed.

15. The method of claim 1 comprising combining a first polymeric or pre-polymeric composition with a second polymeric or pre-polymeric composition to form a reaction mixture, said method comprising combining at least one of said polymeric or pre-polymeric compositions with said microparticles prior to combining said first and second polymeric or pre-polymeric compositions together.

16. The method of claim 15 comprising measuring said electromagnetic characteristic of said microparticles in said reaction mixture.

17. The method of claim 15 comprising combining both of said polymeric or prepolymeric compositions with said microparticles.

18. The method of claim 15 wherein said microparticles in said first polymeric or prepolymeric compositions are different from said microparticles in said second polymeric or prepolymeric composition.

19. The method of claim 15 comprising combining said microparticles with one of said polymeric or pre-polymeric compositions and measuring said electromagnetic characteristic of said reaction mixture to determine the ratio of said first and second polymeric or pre-polymeric compositions to each other.

20. The method of claim 1 wherein said polymeric composition comprises an adhesive composition.

21. The method of claim 1 comprising depositing said admixture on a substrate and measuring the electromagnetic characteristic of said microparticles to determine the amount of said admixture deposited on said substrate.

22. The method of claim 1 wherein said polymeric composition is selected from the group consisting of epoxy resins, polyurethanes, acrylates, and silicone rubbers.

23. The method of claim 1, wherein said electromagnetic characteristic measured is the dielectric constant.

24. The method of claim 1, wherein said electromagnetic characteristic measured is the magnetic permeability.

25. The method of claim 1, wherein said electromagnetic characteristic measured is the inductive reactance.

26. The method of claim 1, wherein said electromagnetic characteristic measured is inductance.

27. The method of claim 1, wherein said electromagnetic characteristic measured in capacitance.

28. A method for measuring the quantity of a polymeric or pre-polymeric composition within a given volume comprising the steps of:

(a) combining said polymeric or pre-polymeric composition with a plurality of coated glass bubble microparticles, where said coating is ferromagnetic, ferrimagnetic, or electrically conductive, to form an admixture in which said microparticles are substantially uniformly dispersed throughout said composition, said microparticles having a detectable electromagnetic characteristic which correlates with the amount of said composition within a given volume; and (b) measuring said electromagnetic characteristic of said microparticles to determine said quantity of said composition within a given volume.

* * * * *